United States Patent [19]

Connor

[11] 4,227,535

[45] Oct. 14, 1980

[54] PROCTOLOGIC DEVICE FOR THE THERAPEUTIC TREATMENT OF HEMORRHOIDS

[75] Inventor: Gerald I. Connor, Spokane, Wash.

[73] Assignee: Bio-Tronics, Inc., Spokane, Wash.

[21] Appl. No.: 26,036

[22] Filed: Apr. 2, 1979

[51] Int. Cl.³ .............................................. A61F 7/12
[52] U.S. Cl. ................................ 128/401; 128/303.12; 219/494; 219/504; 340/573; 340/532; 340/599
[58] Field of Search .................... 128/401, 788, 34, 1, 128/1 B, 395, 303.17, 303.1, 399, 400, 402; 219/491, 494, 499; 340/573, 599, 532

[56] References Cited

U.S. PATENT DOCUMENTS

| | | | |
|---|---|---|---|
| 1,272,469 | 7/1918 | Lidberg | 128/303.12 |
| 1,280,052 | 9/1918 | Lidberg | 128/303.1 |
| 1,615,828 | 2/1927 | Chesney | 74/167 |
| 1,964,732 | 7/1934 | Homan | 128/341 X |
| 2,074,634 | 3/1937 | Ackermann | 128/401 |
| 2,095,678 | 10/1937 | Slutz et al. | 219/21 |
| 3,170,465 | 2/1965 | Henney et al. | 128/401 |
| 3,667,476 | 6/1972 | Muller | 128/399 |
| 3,698,394 | 10/1972 | Piper | 128/303.1 |
| 3,789,853 | 2/1974 | Reinhard | 128/399 |
| 3,820,099 | 6/1974 | Vogt | 340/662 |
| 3,902,502 | 9/1975 | Liss | 128/422 |
| 3,911,924 | 10/1975 | Zimmer | 128/303.1 |
| 3,938,526 | 2/1976 | Anderson et al. | 128/303.1 |
| 4,142,529 | 3/1979 | Latenser et al. | 128/401 |

FOREIGN PATENT DOCUMENTS 109175 12/1939 Australia .
1304740 8/1962 France .

*Primary Examiner*—Robert W. Michell
*Assistant Examiner*—Arthur S. Rose
*Attorney, Agent, or Firm*—Wells, St. John & Roberts

[57] ABSTRACT

A proctologic device is described for therapeutically treating hemorrhoids extending from the anal canal wall of a patient. The device includes an anal canal appliance for intimately contacting the anal canal wall and hemorrhoids. The appliance has sufficient length to extend from the anus to the rectum and sufficient diameter to intimately contact the wall tissues without overly stretching the sphincter muscles. The appliance contains an internal electrical resistor for generating heat in response to the application of electrical energy and a temperature transducer for sensing the temperature of the appliance in the anal canal. The device has a portable case containing an electrical energy storage battery and a control circuit for controlling the application of the electrical energy to the resistor to maintain the temperature of the appliance above body temperature. The control circuit has safety network for discontinuing the application of heat to the appliance should the sensed temperature fall below a preset low temperature or go above a preset elevated temperature.

13 Claims, 3 Drawing Figures

PROCTOLOGIC DEVICE FOR THE THERAPEUTIC TREATMENT OF HEMORRHOIDS

BACKGROUND OF THE INVENTION

This invention relates to devices for the therapeutic treatment of hemorrhoids. It has been estimated that approximately one third of the adults in the United States shall at one time or another have a hemorrhoidal condition that is discomforting and quite painful. It appears that hemorrhoids are more numerous in high stress societies.

Anatomically, hemorrhoids are caused by the swelling and thrombosis of a large plexus of veins in the anal canal followed by edema. Frequently hemorrhoids are considered primarily as varicose veins and their associated effects and disruptions in the anal-rectal canal. In the formation of hemorrhoids, the veins become varicose and the valves of the veins become incompetent through mechanical or vascular hydraulic stresses in excess of the elastic limits of the veinal structure. Causes of hemorrhoids are generally attributed to chronic constipation, irregularity of bowel evacuation, poor dietary habits and pregnancy-induced interference with the venous return flow due to fetal pressures against the pelvic area.

Occasionally hemorrhoids may be accompanied by fissures or cracks in the anal cavity, the base of which becomes secondarily infected, causing bleeding and substantial pain.

Hemorrhoids are generally diagnosed by symptoms or by their appearance in a rectal examination. The formation of hemorrhoids generally involves swelling about the anus which may becomes more pronounced on bowel evacuation. With a chronic case of hemorrhoids, bowel evacuation becomes extremely painful and frequently results in rectal bleeding.

Unless the hemorrhoids have reached an acute stage, treatment is generally accompanied with attention to one's diet, bowel habits and less stressful activity. Frequently a treating physician will recommend that the patient be administered sitz baths three or four times a day in water as hot as a patient can comfortably tolerate. Frequently hydrophilic, bulk stool formers such as "Metamucil" are prescribed to assist in the bowel evacuation process. Acute hemorrhoids frequently require rubber band lagations and some forms of surgery.

A device for the therapeutic treatment of hemorrhoids is described in U.S. Pat. No. 4,142,529 granted Mar. 6, 1979 entitled "Process and Device for the Therapeutic Treatment of Hemorrhoids". Although the device described in such patent and patent application operates satisfactorily, the object of this invention is to provide a much improved device that is safer and more accurate.

These and other objects and advantages of this invention will become apparent upon reading the following detailed description of a preferred and alternate embodiment.

BRIEF DESCRIPTION OF THE DRAWINGS

A preferred and alternate embodiment of this invention is illustrated in the accompanying drawings, in which.

DETAILED DESCRIPTION OF A PREFERRED EMBODIMENT

Figure 1:
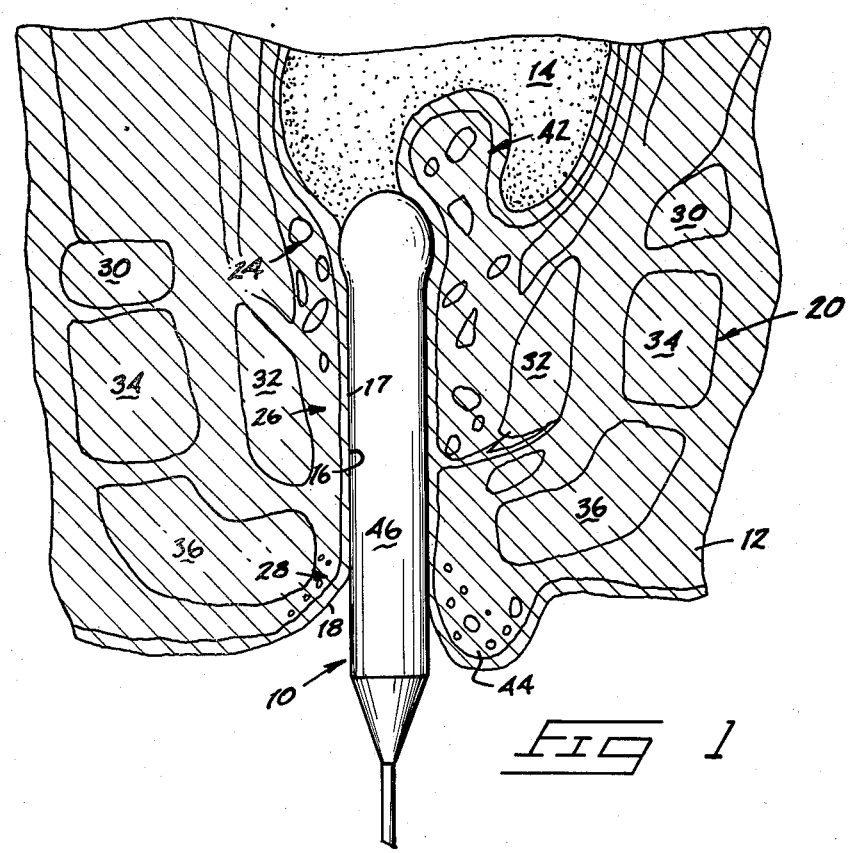
FIG. 1 is a diagrammatical cross-sectional view of the rectal region of a human anal canal showing the anal canal in a nondilated condition with an appliance of the proctologic device inserted therein.

Referring now in detail to the drawings, there is illustrated in FIG. 1 a proctologic device 10 for the therapeutic treatment of hemorrhoids. FIG. 1 shows in diagrammatical cross-section, a portion of the rectal region 12 of a human being. FIG. 1 shows an undilated rectal region 12 with an element of the device inserted therein.

To understand this invention, it is desirable to be acquainted with the anatomical structure of the human rectal region 12. The rectal region 12 illustrated shows a lower portion of a rectum 14 with an anal canal 16 extending from the rectum 14 to an anus 18 that is recessed within an intergluteal cleft between the buttocks. The anal canal 16 has a mucoid surface wall 17 extending from the rectum 14 to the anus 18. The canal wall 17 transforms from a mucous membrane at the rectum 14 to an epidermal surface at the anus 18. The wall 17 is surrounded by the sphincter muscles 20.

The anal canal 16 includes an internal hemorrhoidal plexus region 24, a musculus submucoasae ani region 26 and an external hemorrhoidal plexus region 28. The sphincter muscles are subdivided into a deep external sphincter muscle 30 and an internal sphincter muscle 32, a superficial external sphincter muscle 34 and a subcutaneous external sphincter muscle tissue 36. Internal hemorrhoids 42 are formed at the internal hemorrhoidal plexus region 24 by thrombosis of the vein structure followed by edema. Likewise, when the vein structure of the external hemorrhoidal plexus region 28 becomes varicosed or abnormally dilated (thrombosis) then an external hemorrhoid 44 is formed. The presence of internal and external hemorrhoids 42 and 44 generally cause pain, itching and rectal bleeding particularly during bowel evacuation. The proctologic device 10 is provided to therapeutically treat the hemorrhoids to at least provide temporary relief from such discomfort.

The proctologic device 10 includes an anal canal appliance 46 for positioning within the anal canal 16 as illustrated in FIG. 1. The proctologic device 10 includes a portable control case (not shown) that may be carried or held by the patient himself during the therapeutic treatment process. The portable case contains an electrical storage battery 50 for generating electrical energy. A cable means 52 is connected to the appliance 46 at one end with the other end connectable to the control case for transmitting electrical energy from the storage battery 50 to the suppository appliance 46 to generate internal heating of the appliance 46 for direct physical contact therapeutic treatment of the canal 16.

Figure 2:
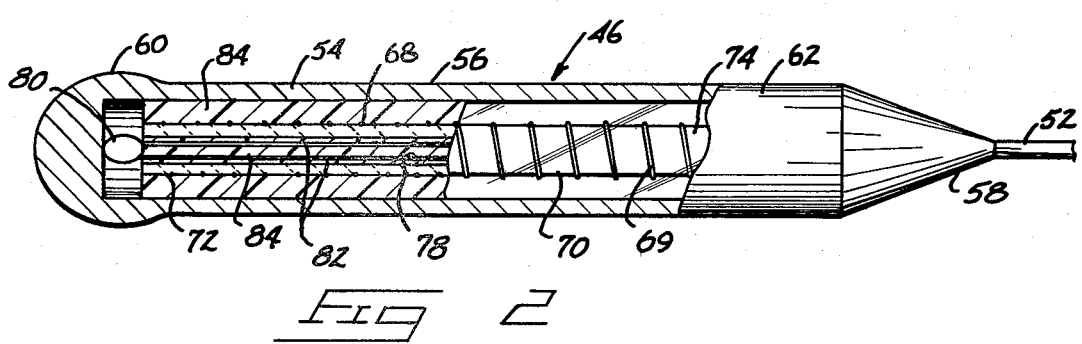
FIG. 2 is a fragmentary longitudinal cross-sectional view of the appliance illustrated in FIG. 1.

The appliance 46 (FIG. 2) includes a cylindrical shell or envelope 54 having a central cylindrical portion 56 that extends from a rear end portion 58 to a front end portion 60. The front end portion 60 is bulbous in shape with the distal tip thereof in the form of a hemisphere. Preferably the envelope 54 is constructed of aluminum. Such metal may be coated with materials such as teflon and polyethylene. The envelope 54 has an exterior heat transfer surface 62 for intimately contacting the tissues of the anal canal 16. To obtain and maintain intimate contact with the anal canal tissues, including the hemorrhoids 42 and 44, it is preferable that the envelope 54 have a length sufficient to extend totally from the anus 18 through the anal canal 16 to the rectum 14. Preferably the central cylindrical portion 56 has a diameter of between five millimeters and ten millimeters inclusive. The bulbous front end portion 60 has a diameter that is between 105% and 130% of the diameter of the central portion 56. The enlarged front end portion 60 assists in maintaining the appliance in the anal canal. The sphincter muscles have a mutual tendency to progressively contract to expel material from the canal. The enlarged front end portion 60 provides additional resistance countering the expelling forces of the sphincter muscles to hold the appliance in the anal canal.

The appliance 46 includes an electrical resistor heating element 68 preferably of a cylindrical type that is concentrically mounted within the envelope 54 for generating internal heat within the envelope 54. Preferably the resistor heating element 68 should have an ohm rating of between 1 and 100 ohms and a power rating at less than 2 watts. The resistor element 68 is preferably formed with a resistive wire 69 helically wound on a cylindrical insulative core 70. The core 70 has a cylindrical outer surface to receive the helically wound electrical wire 69 between core ends 72, 74. The core 70 is preferably constructed of a highly electrical and heat insulative material such as refractory ceramic. The core 70 preferably has an inner pathway 78 extending between the ends 72, 74.

The appliance 46 also includes a temperature transducer 80 for producing an electrical signal representing an analog of the temperature of the heat transfer surface 62. The transducer 80 is preferably mounted in intimate contact with the front end portion 60 to accurately sense the temperature of the envelope. The insulative core 70 thermally insulates the transducer 80 from the resistor element 68 to prevent the resistor element 68 from directly heating the transducer. Preferably the temperature transducer 80 is a thermistor having either a positive temperature coefficient (PTC) or a negative temperature coefficient (NTC). Leads 82 extend from the transducer 80 at the front end portion 60 preferably through the inner pathway 78 to the rear end portion 58.

The resistor element 68 and the temperature transducer 80 are coaxially mounted in the envelope using a moisture resistant mounting or encapsulating material 84 that is electrically nonconductive. Preferably the material 84 is relatively good heat conductor so as to transfer heat from the electrical resistor element 68 to the envelope 54. Preferably the material is a plastic epoxy material. The resistor element 68 has leads 86 that extend from the resistor element 68 to the rear end portion 58.

The cable means 52 includes a flexible electrical cord that extends from the rear end portion 58 of the appliance to the control case. The opposite end of the electrical cord has an electrical connector 88 for releasably mating with a complementary electrical receptacle 90 at the case.

Figure 3:
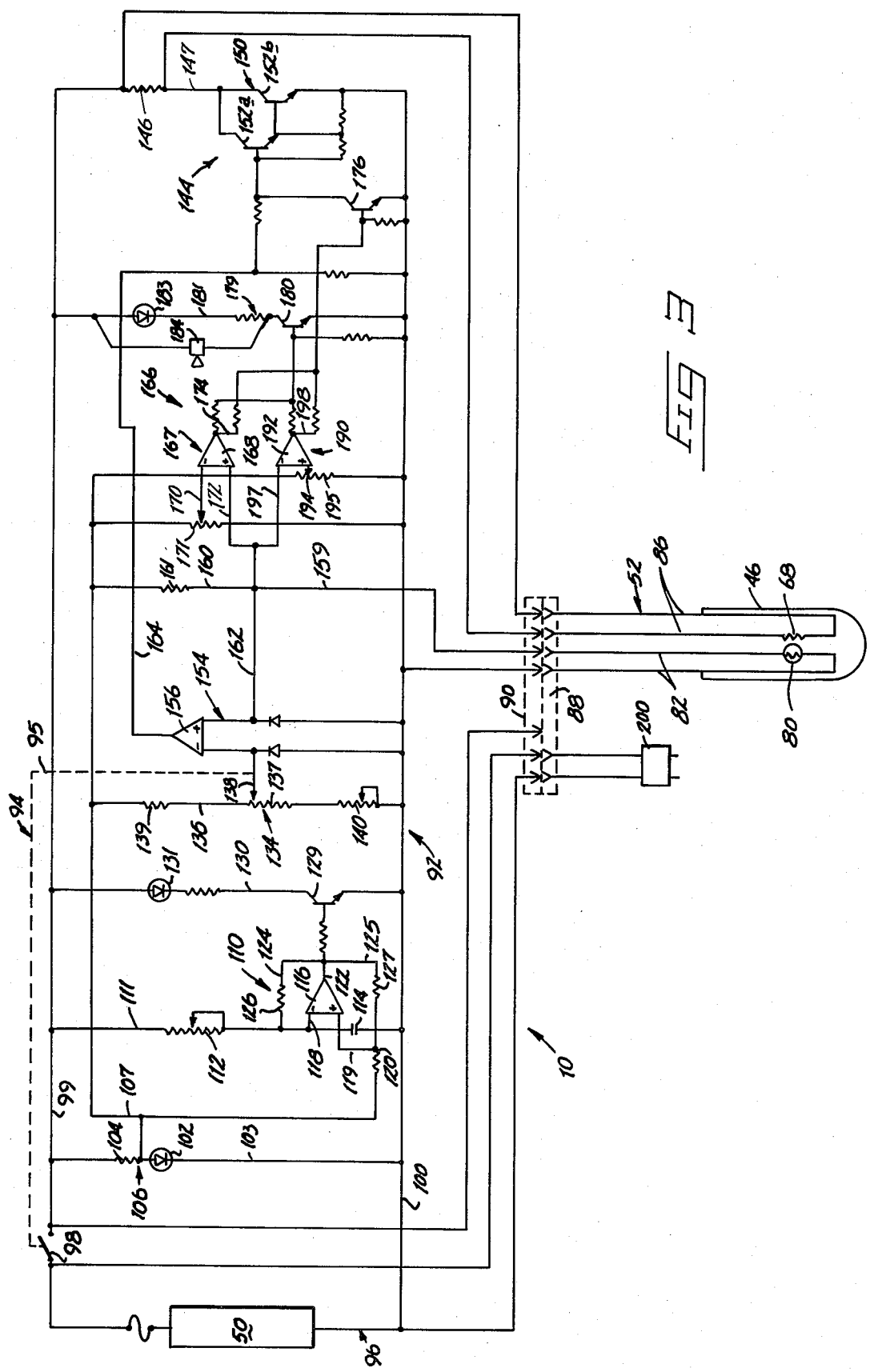
FIG. 3 is an electrical schematic view of an embodiment of the proctologic device.

The proctologic device 10 further includes a control means 92 (FIG. 3) for controlling the application of electrical energy from the storage battery 15 through the cable means 52 to the appliance 46. The control means 92 enables the patient to control the amount of electrical energy applied to the appliance 46 to heat the appliance 46 above the body temperature to a preset temperature and to maintain the temperature of the appliance 46 at the preset temperature to relax the sphincter muscles. Such therapeutic treatment facilitates the opening of the vascular channels of the hemorrhoids to relieve discomfort and facilitates shrinkage of the hemorrhoids.

The control means 92 includes a patient operating means 94 that enables the patient to set and adjust the temperature of the appliance 46. In a preferred embodiment, the patient operating means 94 includes a control knob 95 that is illustrated abstractly as a dotted line in FIG. 3.

Control means 92 includes a power supply network 96 that is connectable to the electrical storage battery 50. The network 96 includes an on/off switch 98 that is controlled by the control knob 95 to enable the patient to initiate and terminate the therapeutic treatment when desired. The power supply network 96 includes unregulated power supply lines 99 and 100. The power supply network 96 includes a visual indicator 102 that is mounted in a line 103 between lines 99, 100 for presenting a visual indication when the on/off switch 98 is "on". The visual indicator 102 is preferably a light emitting diode (LED). A resistor 104 is mounted in line 103 in series with the light emitting diode 102 for regulating the current through diode 102.

The control means 92 includes a voltage regulation network 106 that has a line 107 tapped into line 103 between the resistor 104 and the diode 102. The diode 102 maintains a rather constant voltage drop and serves as a useful voltage reference device. Tap line 107 consequently exhibits a rather constant voltage and is utilized as a regulated voltage supply line to the more voltage sensitive circuits.

The control means 92 further includes a voltage monitoring network 110 for monitoring the voltage of the power supply 50 and to provide a physical warning to the patient should the voltage of the batteries 50 fall below a desired level. The voltage monitoring network 110 includes an unregulated voltage line 111 having a potentiometer or resistor 112 mounted therein in series with a capacitor 114. The network 110 includes a voltage comparator 116 that has an input line 118 and a reference line 119. Line 107 is connected to line 119. Resistors 120 and 127 are mounted in lines 107 and 125 respectively for providing a regulated reference voltage to the voltage comparator 116.

The voltage comparator 116 has an output line 122. The voltage comparator 116 further includes a feedback loop 124 interconnecting the output line 122 with the input line 118. A second feedback loop 125 connects the output line 122 to the reference line 119. Resistors 126 and 127 are mounted in the respective feedback loops 124 and 125. The threshold voltage for the system is set by the potentiometer or resistor 112. When the voltage as sensed on the input line 118 falls below the voltage as sensed on the reference line 119, the voltage comparator 116 is activated to generate an output signal on line 122. The output signal 122 is fed back to the input line 118. However, because of the capacitor 114 the output signal is retarded to the input line 116 through the resistor 126 and the capacitor 114. Likewise, the output signal is applied through the feedback loop 125 to the reference line 119 which additionally increases the reference voltage. As the voltage builds up on line 118 the input voltage will exceed the reference voltage to deactivate the voltage comparator 116 to discontinue the output signal on line 122. When the output signal on line 122 is discontinued, then the input voltage on line 118 will gradually decay and fall below the reference line voltage again activating the voltage comparator 116. The voltage comparator 116 will continue to oscillate as long as the voltage of the batteries 50 is below the preset value as set by the potentiometer or resistor 112.

The output line 122 of the voltage comparator 116 is connected to a transistor switch 129 mounted in an unregulated voltage line 130. A warning device 131 is mounted in the line 130 and is activated when the transistor switch 129 is turned "on" to energize the warning device. In a preferred embodiment, the warning device 131 is an LED providing a visual indication to the patient that the voltage from the batteries 50 is below a desired level. The oscillation of the voltage comparator 116 will cause the LED 131 to blink "on" and "off" to obtain the patient's attention.

The control means 92 includes a temperature selection network 134 for enabling a patient to select a desired temperature for the appliance 36. The network 134 includes a regulated voltage line 136 extending therefrom to form one balance leg of a Wheatstone bridge. A bridge resistor 139 is mounted in the line 136 forming one leg of the bridge. A second bridge resistor 140 is mounted in the line 136 forming a second leg of the bridge. The potentiometer 137 adjusts the resistance ratio in the legs on one side of the bridge. The bridge resistor 140 is preferably selected to limit the temperature selected by the operator.

Control means 92 includes an energy regulating network 144 that is responsive to the temperature selection network 134 for controlling the application of electrical energy from the battery 50 to the appliance 46. In a preferred embodiment the energy control network 144 includes an isolation resistor 146 mounted in unregulated voltage line 147. Additionally, a solid state electrical switch 150 is mounted in the line 147 for applying electrical energy to the appliance 46. In a preferred embodiment electrical switch 150 includes a Darlington transistor pair 152a and 152b which may be triggered to control the application of electrical energy to the resistor element 68. The electrical switch 150 is controlled by a bridge circuit 154 that includes a voltage comparator 156. In the bridge circuit 154 the temperature transducer 80 forms the variable resistor in a third leg or node line 159 of the bridge. Bridge circuit 154 includes a fourth leg or node line 160 that has a resistor 161 to complete the bridge. Node line 159 and 160 intersect with a balance line 162 that is fed to one side of the voltage comparator 156. The voltage comparator 156 compares the voltage as sensed between the tap (reference) line 138 and the input line 162. The voltage comparator 156 has an output line 164 that is connected to the Darlington transistor pair 152a and 152b for triggering the electrical switch 150.

The voltage comparator 156 will sense when there is an imbalance between the resistant ratios in the bridge circuit to turn the voltage comparator "on" and causes the electrical switch 150 to conduct. When the resistant ratios are substantially equal the voltage comparator 156 changes state causing the electrical switch 150 to discontinue the application of electrical energy to the heating element 68. The system rapidly "hunts" about the temperature set point of the tap line 138 during steady state operation. Cooling is always the passive mode and heating is always the active mode. The bridge circuit 154 may be easily modified to accomodate a positive temperature coefficient thermistor 80 to operate the electrical switch 150.

Control means 92 includes a temperature safety network 166 that is responsive to the temperature sensed by transducer 80 for turning the system off should the temperature sensed by the transducer 80 exceed certain preset temperature values. The temperature safety network 166 includes a high temperature circuit 190 having a voltage comparator 192. One side of the comparator 192 is supplied by a voltage reference line through a resistor 194. An input line 197 is connected to node line 159 for providing a temperature signal to the other side of the comparator. The comparator 192 includes an output line 198 that controls a shunt transistor switch 176 for deactivating the electrical switch 150. When the temperature as sensed by the transducer 80 exceeds a preset value determined by the setting of the resistor 194 the voltage comparator 192 is turned "on" to activate the transistor shunt switch 176 to shunt any signal on line 164 to ground to effectively turn off the electrical switch 150 and prevent electrical energy from being supplied to the resistor element 68.

The temperature safety network 166 further includes a warning circuit 179 that has a transistor switch 180 mounted in an unregulated voltage line 181. Visual warning device 183 and audible warning device 184 are mounted in series with the transistor switch 180 to be turned "on" when transistor switch 180 is activated. The activation of voltage comparator 192 turns "on" the transistor switch 180 to energize the visual warning device 183 and the audible warning device 184 to alert the patient that the heating element 68 is above a safe temperature. In the preferred embodiment the visual warning device 183 is a light emitting diode.

The temperature safety network 166 further includes a low temperature circuit 167 that has a voltage comparator 168. A voltage reference line 170 is connected to one side of the voltage comparator utilizing a resistor 171. An input line 172 is connected to the other side of the voltage comparator for applying the signal from the transducer 80. The voltage comparator 168 includes an output line 174 that is connected to the shunt transistor 176 and the warning transistor switch 180. When the voltage comparator 168 is high, the shunt switch 176 is closed to shunt the signal on line 164 to effectively turn "off" the electrical switch 150. When the transistor switch 180 is energized the warning devices 183 and 184 are activated. The resistor 171 is adjusted to provide a voltage that represents a preselected low temperature below normal body temperature which would indicate that there is a malfunction in the system. For example, should an electrical fault or open circuit occur, it would discontinue or provide a very high value signal from the temperature transducer 80 which would be sensed by the voltage comparator 168 to turn "off" the device.

In the preferred embodiment, the safety network 166 provides a temperature window for controlling the device to deactivate the application of electrical energy should the temperature as sensed by the transducer 80 fall outside the boundary of the window as set by the resistors 171 and 195.

Additionally the device 10 includes a battery recharging circuit 200 that may be utilized for recharging the battery 50. The recharging circuit 200 has a similar electrical connector as electrical connector 88. Such a technique provides a safety feature so that either the battery recharger circuit 200 may be connected to the electrical receptacle 90 or the appliance 46, but not both.

During the operation of the proctologic device 10, the appliance 46 is placed in the anal canal with the appliance 46 extending through the anal canal with the front end portion 60 communicating with the rectum 14 so that the entire anal canal 16 is in intimate contact with the heat transfer surface 62 including the internal hemorrhoid 42 and the external hemorrhoid 44.

The appliance 46 is internally heated to a temperature set by the patient above the patient's body temperature. The temperature of the heat surface 62 is then controlled by the control means 54. The temperature of the surface 62 is sensed by the transducer 80. Should for some reason a malfunction occur or overheating, the temperature safety network 166 will discontinue the application of electrical energy to the appliance 46 so as not to injure the patient.

It should be understood that the above described embodiment is simply illustrative of the principles of this invention and numerous other embodiments may be readily devised by those skilled in the art without deviating therefrom. Therefore only the following claims are intended to define this invention.

What I claim is:

1. A proctologic device for the therapeutic treatment of external and/or internal hemorrhoids projecting from the wall of a patient's anal canal which extends from the anus to the rectum and is surrounded by sphincter muscles; comprising:

an anal canal appliance for insertion into the anal canal through the anus;

said appliance having an elongated cylindrical body with an external heat transfer surface extending from a front end to a rear end for intimately contacting the anal canal wall and the projecting hemorrhoids;

said external heat transfer surface having a diameter sufficient to effectively transfer heat from the heat transfer surface to the anal canal wall and the hemorrhoids without painfully stretching the sphincter muscles;

said appliance having an electrical resistor heating element mounted internally within the cylindrical body for converting electrical energy to thermal energy to heat the heat transfer surface;

a source of electrical energy;

cable means extending between the source and the appliance for operatively connecting the source to the electrical resistor heating element;

a temperature transducer mounted in the appliance for sensing the temperature of the external heat transfer surface and for producing an electrical temperature signal corresponding to the temperature of the external heat transfer surface;

control means operatively connected to the source and responsive to the electrical temperature signal for automatically regulating the amount of electrical energy applied to the electrical resistor heating element to heat the external heat transfer surface and to maintain the external heat transfer surface at preset temperature above body temperature;

safety network means independent of said control means with a high temperature circuit responsive to the electrical temperature signal for automatically terminating the application of electrical energy to the electrical resistor heating element should the temperature sensed by the temperature transducer exceed a preset elevated temperature;

wherein the high temperature circuit includes a voltage comparator for receiving the electrical temperature signal and in comparing the voltage of the electrical temperature signal with a preset voltage of a reference signal corresponding to the preset elevated temperature to terminate the application of electrical energy to the electrical resistor heating element when the differential voltage between the electrical temperature signal and the reference signal reaches a preset value.

2. The proctologic device as defined in claim 1 wherein the safety network includes a low temperature circuit for automatically terminating the application of electrical energy to the electrical resistor heating element should the temperature sensed by the temperature transducer fall below a preset low temperature.

3. The proctologic device as defined in claim 2 wherein the control means includes an electrical switch, operatively interconnecting the source and the electrical resistor heating element and wherein the low temperature circuit includes a voltage comparator for receiving the electrical temperature signal and comparing the voltage of the electrical temperature signal with a preset voltage of a reference signal and for actuating the electrical switch to discontinue the application of the electrical energy to the electrical resistor heating element when the differential voltage between the electrical temperature signal and the reference signal approaches a preset value.

4. The proctologic device as defined in claim 1 wherein the control means includes an electrical switch operatively interconnecting the source and the electrical resistor heating element and wherein the safety network includes a low temperature circuit responsive to the electrical temperature signal and wherein the high temperature circuit and the low temperature circuit include respective voltage comparators operatively connected to the electrical switch for comparing the voltage of the electrical temperature signal with preset voltages of respective reference signals and for actuating the electrical switch to discontinue the application of the electrical energy to the electrical resistor heating element when the differential voltages between the electrical temperatures and the respective reference signals approach preset values.

5. The proctologic device as defined in claim 1 wherein the source of electrical energy includes portable batteries for supplying electrical energy and wherein the device further includes battery voltage monitoring means with warning means for generating a warning to the user when the battery voltage falls below a preset voltage.

6. The proctologic device as defined in claim 5 wherein the warning device includes a light source and wherein the battery voltage monitoring means includes an electronic network for periodically turning the light source off and on in a blinking fashion to warn the user when the battery voltage falls below a preset voltage.

7. The proctologic device as defined in claim 1 wherein the source of electrical energy includes portable batteries for supplying electrical energy and wherein the device further comprises a voltage regulation means operatively connected to the portable batteries for producing a regulated control signal having a preset voltage for utilization by the control means to control the application of the electrical energy to the electrical resistor heating element.

8. The proctologic device as defined in claim 7 wherein the voltage regulation means includes a manually operable electrical switch to turn the device on and off and wherein the voltage regulation means further includes a visual display network having a preset value resistor and a light source mounted in series with the manually operable electrical switch in which the light source is illuminated when the manual electrical switch is closed and wherein the light source is a light emitting diode in which the resistance of the light emitting diode in which the voltage drop across the light emitting diode is substantially constant and wherein the voltage regulation means includes a regulated voltage network in parallel with the light emitting diode for producing the regulated control signal with a preset voltage corresponding to the voltage drop across the light emitting diode.

9. A proctologic device for the therapeutic treatment of external and/or internal hemorrhoids projecting from the wall of a patient's anal canal which extends from the anus to the rectum and is surrounded by sphincter muscles; comprising;

an anal canal appliance for insertion into the anal canal through the anus;

said appliance having an elongated cylindrical metal envelope with an external heat transfer surface extending from a front end to a rear end for intimately contacting the anal canal and the projecting hemorrhoids;

said external heat transfer surface having a diameter sufficient to expand the anal canal and effectively transfer heat from the heat transfer surface to the anal canal wall and the hemorrhoids without painfully stretching the sphincter muscles;

said appliance having an electrical resistor heating element mounted internally within the cylindrical metal envelope for converting electrical energy to thermal energy;

said electrical resistor heating element comprising a cylindrical thermal insulative ceramic core mounted coaxially within the cylindrical metal envelope and an electrical resistor conductive material mounted on the insulative core;

a temperature transducer in direct engagement with the front end of the metal envelope to produce an electrical temperature signal corresponding directly to the temperature of the external heat transfer surface;

wherein the thermal insulation core is mounted within the metal envelope interposed between the electrical resistor conductive material and the transducer to form a thermal barrier to prevent direct heat transfer from the electrical resistor conductive material and the temperature transducer to minimize temperature sensing error;

a source of electrical energy;

a cable means extending between the source and the appliance for operatively connecting the source to the electrical resistor heating element;

control means operatively connected to the electrical energy source and responsive to the electrical temperature signal for automatically regulating the amount of electrical energy applied to the electrical resistor heating element to heat the external heat transfer surface and to maintain the external heat transfer surface at a preset temperature above body temperature to thereby relax the sphincter muscles and to facilitate the opening of vascular channels of the homorrhoids to facilitate shrinkage of the hemorrhoids.

10. The proctologic device as defined in claim 9 wherein the cylindrical insulative core is constructed of a ceramic material that is highly heat insulative to minimize direct heating of the temperature transducer from the electrical resistive wire.

11. The proctologic device as defined in claim 9 wherein the front end of the anal canal envelope is bulbous in shape to assist in the retention of the appliance in the anal canal.

12. The proctologic device as defined in claim 11 wherein the bulbous front end of the envelope has a diameter that is between 105% and 130% of the diameter of a central portion of the appliance.

13. The proctologic device as defined in claim 9 wherein the temperature transducer extends through the cylindrical insulative core and engages the front end of the envelope.

* * * * *